(12) United States Patent  (10) Patent No.: US 8,192,408 B2
Nazzaro et al.  (45) Date of Patent: Jun. 5, 2012

(54) OCULAR TROCAR ASSEMBLY

(75) Inventors: Martin Nazzaro, Quincy, MA (US);
Hong Guo, Wayland, MA (US); Ron LeBlanc, Hopedale, MA (US); Josh York, Ipswich, MA (US)

(73) Assignee: pSivida US, Inc., Watertown, MA (US)

( * ) Notice: Subject to any disclaimer, the term of this patent is extended or adjusted under 35 U.S.C. 154(b) by 102 days.

(21) Appl. No.: 12/703,634

(22) Filed: Feb. 10, 2010

(65) Prior Publication Data
US 2010/0234817 A1  Sep. 16, 2010

Related U.S. Application Data

(60) Provisional application No. 61/151,426, filed on Feb. 10, 2009.

(51) Int. Cl.
*A61M 5/32* (2006.01)
(52) U.S. Cl. .......................... 604/272; 604/289; 604/294
(58) Field of Classification Search ........... 604/8, 164.1, 604/272–274, 289, 294
See application file for complete search history.

(56) References Cited

U.S. PATENT DOCUMENTS

| | | | |
|---|---|---|---|
| 4,810,244 | A | 3/1989 | Allen |
| 5,057,082 | A | 10/1991 | Burchette, Jr. |
| 5,370,630 | A | 12/1994 | Smidebush et al. |
| 5,792,099 | A | 8/1998 | DeCamp et al. |
| 7,090,681 | B2 | 8/2006 | Weber et al. |
| 2004/0230183 | A1 | 11/2004 | Breegi et al. |
| 2004/0243101 | A1 | 12/2004 | Gillis |
| 2006/0111605 | A1* | 5/2006 | Larsen et al. ............ 600/1 |
| 2007/0073248 | A1 | 3/2007 | Moenning |
| 2008/0195135 | A1 | 8/2008 | Attinger |

OTHER PUBLICATIONS

International Search Report dated Nov. 30, 2010, Serial No. PCT/US2010/023707.

\* cited by examiner

*Primary Examiner* — Jackie Ho
*Assistant Examiner* — Imani Hayman
(74) *Attorney, Agent, or Firm* — Ropes & Gray LLP

(57) ABSTRACT

The invention provides a trocar assembly for delivering a payload into tissue, such as an eye, comprising a primary housing, a cannula, a payload, an actuator and a trocar.

30 Claims, 2 Drawing Sheets

OCULAR TROCAR ASSEMBLY

RELATED APPLICATIONS

This application claims the benefit of priority to U.S. Provisional Application Ser. No. 61/151,426, filed Feb. 10, 2009, which application is hereby incorporated in its entirety.

BACKGROUND OF THE INVENTION

A primary difficulty in treating diseases of the eye is introducing drugs or therapeutic agents into the eye and maintaining these drugs or agents at a therapeutically effective concentration in the eye for the necessary duration. Systemic administration may not be an ideal solution because, often, unacceptably high levels of systemic dosing are needed to achieve effective intraocular concentrations, with the increased incidence of unacceptable side effects of the drugs. Simple ocular instillation or application is not an acceptable alternative in many cases, because the drug may be quickly washed out by tear-action or pass from the eye into the general circulation. Suprachoroidal injections of drug solutions have also been performed, but again the drug availability is short-lived. Such methods make it difficult to maintain therapeutic levels of drug for adequate time periods.

Efforts to address this problem have lead to the development of drug delivery devices, or implants, which can be implanted into the eye such that a controlled amount of desired drug can be released constantly over a period of several days, or weeks, or even months. Many such devices have been previously reported.

Various sites exist in the eye for implantation of a drug delivery device or implant, such as the vitreous of the eye, anterior or posterior chambers of the eye, or other areas of the eye including intraretinal, subretinal, intrachoroidal, suprachoroidal, intrascleral, episcieral, subconjunctival, intracorneal or epicorneal spaces. Wherever the desired location of implantation, typical methods of implantation all require relatively invasive surgical procedures, pose a risk of excessive trauma to the eye, and require excessive handling of the implant. For example, in a typical method for placement in the vitreous, an incision is made through the sclera, and the implant is inserted into and deposited at the desired location in the vitreous, using forceps or other like manual grasping device. Once deposited, the forceps (or grasping device) is removed, and the incision is sutured closed. Alternatively, an incision can be made through the sclera, a trocar can be advanced through the incision and then the implant can be delivered through the trocar. Similar methods can be employed to deliver implants to other locations, e.g., implantation in the anterior chamber of the eye through an incision in the cornea.

The drawbacks of such techniques for implant delivery are many. Extensive handling of the implant is necessitated in these techniques, creating a risk that the implant will be damaged or contaminated in the process. Many such implants are polymer-based and relatively fragile. If portions of such implants are damaged and broken off, the release profile and/or effective therapeutic dose delivered by the implant once placed will be significantly altered. In addition, achieving reproducible placement from patient to patient can be difficult using these methods. Also of import is that fact that such techniques may require an opening in the sclera large enough to require suturing. Thus, such techniques are typically performed in a surgical setting.

A more facile, convenient, less invasive, and/or less traumatic means for delivering implants into the eye would be desirable.

SUMMARY OF THE INVENTION

The present invention provides methods and apparatus for delivering a payload into tissue, such as an eye.

In one aspect of the invention, a trocar assembly is provided for delivering a payload into tissue, comprising a primary housing, a cannula, a payload, an actuator and a trocar. The cannula defines a lumen and has a proximal portion received in the housing and a distal portion extending from the housing. In certain embodiments, a payload is disposed in an initial position within the housing and in communication with the cannula. The trocar comprises a distal end with a tip for piercing tissue and a proximal end in communication with a shifter for positioning the trocar, wherein, in an extended position, the trocar occupies the lumen and extends past the distal end of the cannula, and, in a retracted postion, the trocar is sufficiently retracted from the lumen such that the payload can pass through the lumen to exit via the distal end of the cannula. The actuator advances the payload through the lumen to exit via the distal portion of the cannula.

In certain embodiments, the trocar is non-coring, such as does not define an open lumen, e.g., is solid and/or otherwise is capable of substantially filling the lumen of the cannula. The trocar may comprise metal such as stainless steel. In certain embodiments, the trocar has a diameter between 0.20 mm and 0.75 mm, such as approximately 0.5 mm. The trocar may, in some embodiments, create a channel from about 20- to about 32-gauge in the tissue, such as a 25-gauge channel in the tissue.

In certain embodiments, the shifter for the trocar comprises a trigger mechanism capable of being activated by a user for extending and retracting the trocar. The assembly may further comprise a lock for locking the trocar in the retracted position.

In certain embodiments, the payload comprises a liquid. In certain embodiments, the payload may comprise a gas. In certain embodiments, the payload may comprise a solid, such as an ocular implant. The payload may comprise a pharmaceutical agent (e.g., a drug or other therapeutic agent) and/or a diagnostic agent. In certain embodiments, the payload resides in a payload receptacle in the housing of the trocar assembly. In certain embodiments, the payload receptacle can be detached from the housing. The payload receptacle may be a cartridge or ampoule. The payload receptacle may be for a single use, refillable and/or sterilizable.

In certain embodiments, the cannula is coupled to the housing of the trocar assembly. The cannula may comprise metal such as stainless steel or a polymeric material such as polyimide and/or polycarbonate.

The invention further provides methods for delivering a payload to a tissue comprising: positioning the distal end of the cannula of the trocar assembly in contact with or adjacent to the tissue; inserting the trocar into the tissue; retracting the trocar; advancing the payload through the lumen; and depositing the payload in the tissue. The trocar may be shifted to the extended position from the retracted position prior to positioning the trocar within the tissue. In certain such embodiments, the trocar occupies the lumen and may extend past the distal end of the cannula in the extended position prior to positioning the trocar within the tissue. Once the trocar is positioned within the tissue, upon retracting the trocar, the distal end of the cannula remains within the tissue. The payload may then be advanced into the tissue by any means such as a plunger, a pump, vibration or an electrostatic gradient. In certain embodiments, wherein the payload is advanced by a plunger, the plunger may be actuated by any means such as by a spring, compressed gas or manual positioning.

DETAILED DESCRIPTION OF THE INVENTION

Figure 1:
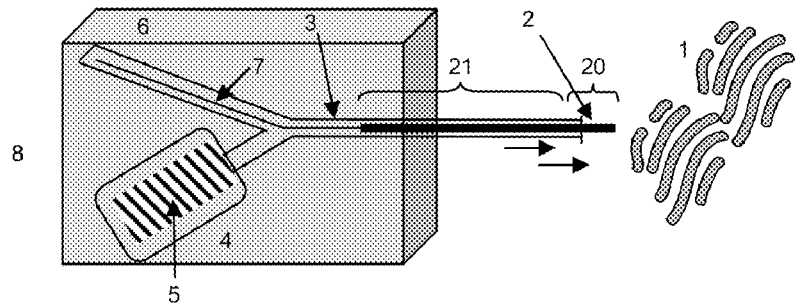
FIG. 1 depicts the trocar assembly 8 according to one embodiment of the present invention adjacent to tissue 1 prior to insertion.
Figure 2:
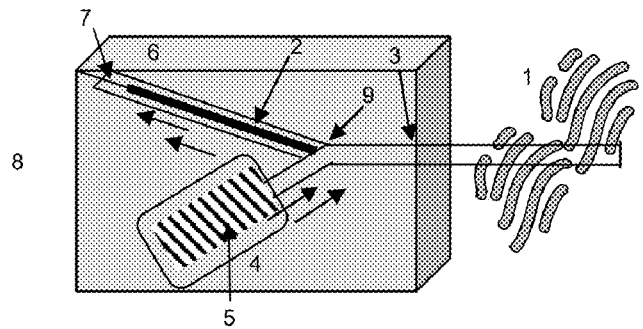
FIG. 2 depicts the trocar assembly 8 and the insertion of the trocar 2 into the tissue 1 and retraction of the trocar 2, leaving the cannula 3 within the tissue 1.
Figure 3:
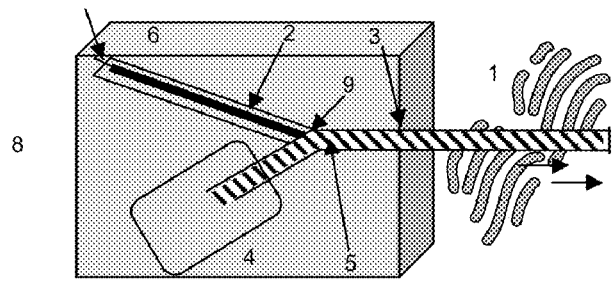
FIG. 3 depicts the payload 5 advancing from the payload receptacle 4, through the cannula 3 and into the tissue 1.

An embodiment of a trocar assembly of the present invention is depicted in FIGS. 1-3. As shown, the trocar assembly 8 includes a primary housing 6 with a cannula 3 and trocar 2 that extends outside of the housing 6. The cannula 3 defines a lumen and has a proximal portion received in the housing 6 and a distal portion extending from the housing 6. The cannula 3 may be integral to or separate from housing 6. The trocar 2 comprises a distal end 20 with a tip for piercing tissue 1 and a proximal end 21 in communication with a shifter 7 for positioning the trocar 2, wherein, in an extended position, the trocar 2 occupies the lumen of the cannula 3 and extends past the distal end of the cannula 3, and, in a retracted position, the trocar 2 is sufficiently retracted from the lumen such that the payload 5 can pass through the lumen to exit via the distal end of the cannula, e.g., to enter the tissue following retraction of the trocar. The payload 5 is stored in the payload receptacle 4 which is coupled to and/or located partially or entirely within the housing 6.

In certain embodiments, the trocar 2 is shifted to the extended position from the retracted position prior to insertion into the tissue 1, as shown in FIG. 1. In certain such embodiments, the trocar may extend past the distal end of the cannula in the extended position prior to insertion into the tissue. In certain such embodiments, the trocar 2 and cannula 3 may be inserted into the tissue 1 in the manner of a needle of a syringe by manual pressure. In certain embodiments, the trocar 2 may be shifted by the shifter 7 to enter the tissue 1 by other means. In some such embodiments, the shifter 7 comprises a trigger mechanism capable of being activated by a user for extending and retracting the trocar 2. The trigger mechanism may retract the trocar 2 following insertion of the cannula 3 into the tissue 1. Upon retracting the trocar, the distal end of the cannula remains within the tissue. The trocar 2 may extend, retract, or extend and retract when the trigger mechanism is activated. In the retracted position, the trocar 2 may be locked in place by a lock 9. The trigger mechanism may function in conjunction with the lock 9 such that when the trigger mechanism is activated the lock 9 releases and the trocar 2 extends. In embodiments where the trigger mechanism activates the trocar 2 to extend and retract, the trigger mechanism may release the lock 9 prior to extending the trocar 9 and lock the trocar 2 in place once the trocar 2 has retracted again. The shifter 7 may be activated by any method known for advancing an object through tissue. Exemplary methods for activating the shifter 7 include a spring, compressed gas, or mechanical gears.

With the trocar 2 in a retracted position, as shown in FIG. 2, and the cannula 3 within the tissue 1, the payload 5 may be advanced by an actuator through the lumen to exit via the distal portion of the cannula 3. The payload 5 may be advanced by any method known for advancing a solid, liquid or gas through a cannula 3. The payload 5 may be advanced from the payload receptacle 4 by an actuator such as a plunger, pump, vibration or electrostatic gradient. In certain embodiments, wherein the actuator is a plunger, the plunger is activated by any of a spring, compressed gas, or manual compression.

To use the trocar assembly for delivering the payload into the tissue of a patient, the trocar assembly is positioned near the desired point of entry into the tissue. The trocar assembly may be mounted on a stand and/or supported by the hand of a user. The patient will typically be under a topical or local anesthetic. The user can then advance the trocar into the tissue and position the cannula at a desired location within the patient's tissue for deposition of the payload. Once the cannula is positioned, the user may prompt the actuator to deliver the payload from the payload receptacle through the lumen and out of the distal end of the cannula. After the payload has been delivered, the cannula is withdrawn from the patient's tissue.

In an exemplary embodiment, the trocar assembly is used to deliver a payload into the eye. The trocar assembly may be used to position the payload at a desired implantation site, e.g., in the vitreous cavity of the eye. For such embodiments, the trocar assembly may be positioned near the eye and the trocar extended through the sclera and into the vitreous of the eye. The cannula can be positioned at a desired position in the vitreous of the eye for placement of the payload. Once the payload is delivered into the eye, the cannula can be withdrawn.

In certain embodiments, the payload comprises a liquid and/or a gas. The payload may comprise a solid, e.g., an ocular implant such as a drug delivery device. Such devices typically can be implanted into any number of locations in tissue and can be designed such that a controlled amount of desired drug or therapeutic can be released over time. The payload may comprise a pharmaceutical agent. In certain embodiments, the payload is a microimplant comprising a therapeutic agent and a polymer. The microimplant can be delivered through a cannula corresponding to 21-gauge cannula or smaller, and therefore has a cross-sectional diameter of 0.66 mm or less. Methods for making microimplants include extrusion methods, injection molding, compression molding and tableting methods. In certain embodiments, the payload resides in a payload receptacle in the housing of the trocar assembly. In certain embodiments, the payload receptacle can be detached from the housing. The payload receptacle may be a cartridge or ampoule. The payload receptacle may be of a single use, refillable and/or sterilizable.

In certain embodiments, the trocar is non-coring, e.g., the trocar does not comprise a lumen. The trocar may comprise metal such as stainless steel. In certain embodiments, the trocar has a diameter between 0.20 mm and 0.75 mm, such as approximately 0.75 mm, approximately 0.60 mm, approximately 0.50 mm, approximately 0.40 mm, approximately 0.30 mm or approximately 0.20 mm. The trocar may, in some embodiments, create a channel from about 16- to about 32-gauge in the tissue, such as from about 16- to about 32-gauge in the tissue, such as about 25-gauge, about 26-gauge, about 27-gauge about 28-gauge, about 29-gauge or about a 30-gauge channel in the tissue.

A typical problem when inserting a trocar with a lumen into any tissue is the phenomena of "coring" of the tissue, where the insertion actually cuts a cylindrical section of tissue that enters the trocar lumen. Such coring, when it occurs in the eye, can exacerbate leakage of eye fluid through the injection site. An alternative is to use a non-coring trocar such as a trocar that is solid or partially solid such that the tip of the trocar does not comprise an opening. In such embodiments, the proximal end of the trocar may comprise a point or a blunt tip. Other traditional methods known in the art for avoiding coring may be used such as deflection of the tip of the trocar or dulling and sharpening portions of the trocar point.

In certain embodiments, the cannula is coupled to the housing of the trocar assembly. The cannula may comprise metal such as stainless steel or a polymeric material such as polyimide, silicone, polycarbonate and/or polyvinyl carbonate. In certain embodiments, cannulas to be used in the present invention are thin-walled. The cannula has an external diameter between 0.25 mm and 1.0 mm, such as approximately 1.0 mm, approximately 0.90 mm, approximately 0.80 mm, approximately 0.70 mm, approximately 0.60 mm, approximately 0.50 mm, approximately 0.40 mm, approximately about 0.30 mm or approximately 0.25 mm. The cannula may, in some embodiments, hold open a channel from about 16- to about 32 gauge in the tissue, such as from about 21- to about 30 gauge in the tissue, such as about 24-gauge, about 25-gauge, about 26-gauge, about 27-gauge, about 28-gauge, about 29-gauge or about a 30-gauge channel in the tissue.

Figure 4:
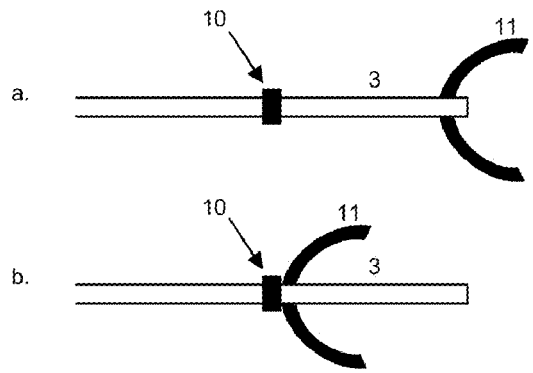
FIG. 4 depicts: a. the cannula 3 of the trocar assembly 8 inserted within the sclera of the eye 11 where the cannula 3 has a section of enlarged diameter 10 relative to other portions of the cannula 3 in which b. the cannula 3 may advance into the eye tissue until the cannula's enlarged diameter section 10 meets the sclera 11 and hinders further advancement of the cannula 3 into the eye.
Figure 5:
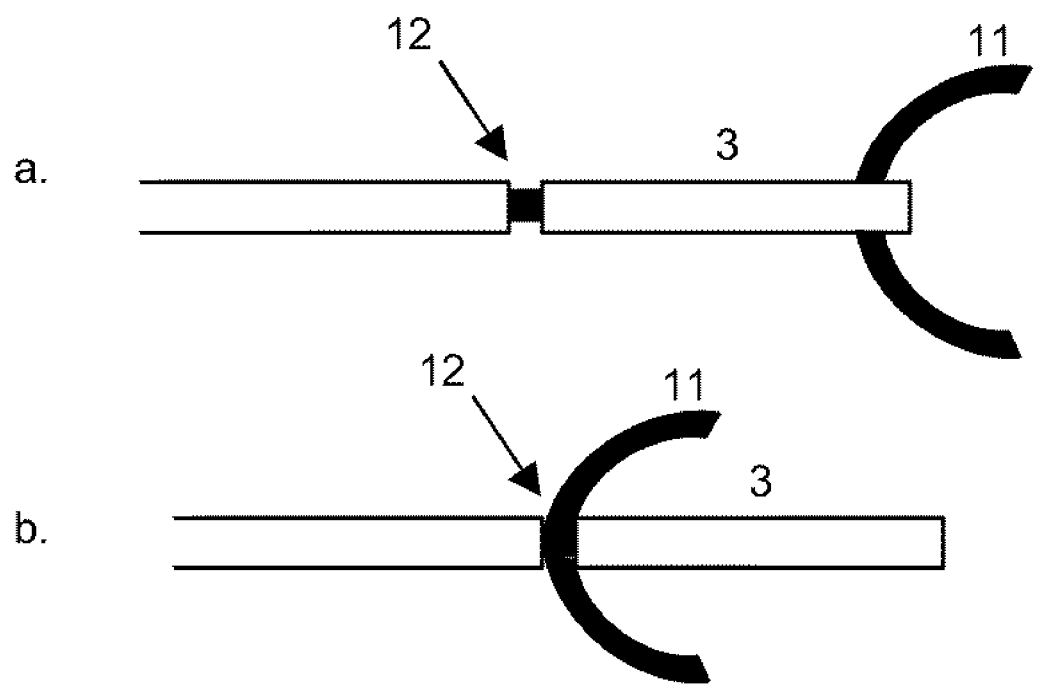
FIG. 5 depicts: a. the cannula 3 of the trocar assembly 8 inserted within the sclera of the eye 11 where the cannula 3 has a section of contracted diameter 12 relative to other portions of the cannula 3 in which b. the cannula 3 may advance into the eye tissue until the cannula's contracted diameter section 12 meets the sclera 11 and hinders further advancement and/or retraction into and/or from the eye.

The cannula of the invention may have a uniform external diameter or the diameter may vary along the length of the cannula. For example, as in FIG. 4a, the cannula 3 may have a section of enlarged diameter 10 relative to other portions of the cannula 3 in which b. the cannula 3 may advance into the eye tissue until the cannula's enlarged diameter section 10 meets the sclera 11 and hinders further advancement of the cannula 3 into the eye (FIG. 4). In other exemplary embodiments, as in FIG. 5a, the cannula 3 has a section of contracted diameter 12 relative to other portions of the cannula 3 in which b. the cannula 3 may advance into the eye tissue until the cannula's contracted diameter section 12 meets the sclera 11 and hinders further advancement and/or retraction into and/or from the eye (FIG. 5). In certain such embodiments, the section of the cannula 3 of enlarged diameter 10 and/or contracted diameter 12 may correspond to a predetermined depth of entry into the tissue and/or a desired implantation depth.

The invention further contemplates the use of cannulas having non-circular cross-sections, including oval or elliptical cross-sections. For such non-circular cross-sectional cannulas, it is desirable that the cross-sectional area correspond to that of a circular cannula having up to a 1.0 mm diameter.

In certain embodiments, the cannula is designed to limit the introduction of air into the eye upon injection of the implant. In an exemplary embodiment, the implant can be positioned proximally to the cannula tip but with sufficient tolerance between the implant and cannula wall to provide for air exhaust past the implant as it is moved through the cannula.

The payload may then be advanced into the tissue by any means such as a plunger, a pump, vibration or an electrostatic gradient. In certain embodiments, wherein the payload is advanced by a plunger, the plunger may be actuated by any means such as by a spring, compressed gas or manual compression.

Additional embodiments provide for safety features which include, among other things, locking mechanisms which prevent reuse of the applicator, gauges to determine the location of the proximal end of the cannula within the tissue and pressure gauges to monitor pressure build-up within tissue, such as the eye.

In addition to delivering implants into the eye, devices as disclosed herein can be used to inject implants into other tissues, and are of particular use where minimal tissue damage is desired, e.g., implantation into the cerebrospinal fluid, the bladder, etc.

EQUIVALENTS

The present invention provides among other things trocar assemblies and methods of use thereof. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

We claim:
1. A trocar assembly for delivering a payload into tissue, comprising:
a primary housing;
a cannula defining a lumen and having a proximal portion received in the housing and a distal portion extending from the housing;
a payload disposed in an initial position within the housing and in communication with the cannula;
an actuator for advancing the payload through the lumen to exit via the distal portion of the cannula;
a trocar comprising a distal end with a tip for piercing tissue and a proximal end in communication with a shifter for positioning the trocar, wherein, in an extended position, the trocar occupies the lumen and extends past the distal end of the cannula, and, in a retracted position, the trocar is sufficiently retracted from the lumen such that the payload can pass through the lumen to exit via the distal end of the cannula.

2. The assembly of claim 1, wherein the trocar is non-coring.

3. The assembly of claim 1, wherein the trocar comprises metal.

4. The assembly of claim 3, wherein the trocar comprises stainless steel.

5. The assembly of claim 1, wherein the shifter comprises a trigger mechanism capable of being activated by a user for extending and retracting the trocar.

6. The assembly of claim 1, further comprising a lock for locking the trocar in the retracted position.

7. The assembly of claim 1, wherein the payload comprises a liquid.

8. The assembly of claim 1, wherein the payload comprises a gas.

9. The assembly of claim 1, wherein the payload comprises a solid.

10. The assembly of claim 1, wherein the distal end of the cannula is coupled to the housing.

11. The assembly of claim 1, wherein the payload comprises a pharmaceutical agent.

12. The assembly of claim 1, wherein the diameter of the trocar is between 0.20 mm and 0.75 mm.

13. The assembly of claim 12, wherein the diameter of the trocar is approximately 0.5 mm.

14. The assembly of claim 1, wherein the trocar creates a channel from about 16- to about 32-gauge in the tissue.

15. The assembly of claim 14, wherein the trocar creates a 25-gauge channel in the tissue.

16. The assembly of claim 1, wherein the cannula comprises metal.

17. The assembly of claim 16, wherein the cannula comprises stainless steel.

18. The assembly of claim 1, wherein the cannula comprises a polymeric material.

19. The assembly of claim 18, wherein the cannula comprises polyimide and/or polycarbonate.

20. The assembly of claim 1, wherein the payload resides in a payload receptacle in the housing.

21. The assembly of claim 20 wherein the payload receptacle is can be detached from the housing.

22. The assembly of claim 21, wherein the payload receptacle is a cartridge or ampoule.

23. The assembly of claim 22, wherein the payload receptacle is any of a single use, refillable and sterilizable.

24. The assembly of claim 1, wherein the tissue comprises an eye.

25. A method for delivering a payload to a tissue comprising:
    placing the distal end of the cannula of the trocar assembly of claim 1 in contact with or adjacent to the tissue;
    inserting the trocar, in the extended position, into the tissue;
    retracting the trocar to the retracted position;
    advancing the payload through the lumen and depositing the payload in the tissue; and
    removing the cannula from the tissue.

26. The method of claim 25, wherein the trocar is shifted to the extended position from the retracted position prior to insertion into the tissue.

27. The method of claim 25, wherein the trocar occupies the lumen and extends past the distal end of the cannula in the extended position prior to insertion into the tissue.

28. The method of claim 25, wherein when the trocar is retracted, the distal end of the cannula remains within the tissue.

29. The method of claim 25, wherein the payload is advanced by any of a plunger, pump, vibration or electrostatic gradient.

30. The method of claim 29, wherein the payload is advanced by a plunger and the plunger is activated by any of a spring, compressed gas, or manual compression.

* * * * *